United States Patent [19]

Hazard et al.

[11] 3,952,013
[45] Apr. 20, 1976

[54] 1-THIACHROMONE-2-CARBOXYLIC ACIDS AND DERIVATIVES

[75] Inventors: Richard Hazard, Cropston; John King, Loughborough, both of England

[73] Assignee: Fisons Limited, England

[22] Filed: Mar. 27, 1974

[21] Appl. No.: 455,348

Related U.S. Application Data

[63] Continuation of Ser. No. 258,752, June 1, 1972, abandoned, which is a continuation-in-part of Ser. No. 10,623, Feb. 11, 1970, abandoned.

[30] Foreign Application Priority Data

Feb. 12, 1969  United Kingdom................. 7467/69
June 8, 1971  United Kingdom............... 19378/71
Nov. 29, 1971  United Kingdom............... 55152/71

[52] U.S. Cl. ..................... 260/327 TH; 260/340.6; 260/340.9; 260/343.2 R; 260/345.2; 260/516; 260/519; 260/520 R; 260/521 R; 260/521 N; 260/521 S; 260/521 P; 260/521 H; 424/275; 424/279; 424/282; 424/283

[51] Int. Cl.²........................................ C07D 335/06

[58] Field of Search.............................. 260/327 TH

[56] References Cited
UNITED STATES PATENTS
2,923,716  2/1960  Bossert ............................. 260/327

*Primary Examiner*—John D. Randolph
*Assistant Examiner*—C. M. S. Jaisle
*Attorney, Agent, or Firm*—Wenderoth, Lind & Ponack

[57] ABSTRACT

Pharmaceutical compounds of formula I,

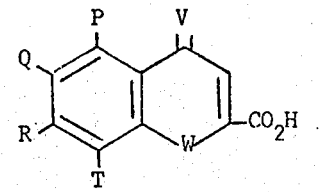

in which
P, Q, R, and T, which may be the same or different, each represent hydrogen, an alkyl, hydroxy, alkoxy, hydroxyalkoxy, alkoxyalkoxy, acetoxy, carboxy, amino, alkylamino, dialkylamino, alkenyl, p-toluenesulphonyloxy, aralkyl, phenyl, nitro, carboxy ester, alkenyloxy or acyl group, none of which groups contain more than 10 carbon atoms or an adjacent pair of P, Q, R and T, together with the adjacent carbon atoms in the benzene ring may form a fused 5 or 6 membered carbocyclic or oxygen containing heterocyclic ring, and
V and W, which are different, each represent oxygen or sulphur.

24 Claims, No Drawings

1-THIACHROMONE-2-CARBOXYLIC ACIDS AND DERIVATIVES

This is a continuation of application Ser. No. 258,752, filed June 1, 1972, which application is in turn a continuation-in-part of application Ser. No. 10,623, filed Feb. 11, 1970, both now abandoned.

This invention relates to new compounds and to methods of their preparation. The invention also relates to new compositions.

According to our invention we provide compounds of formula I,

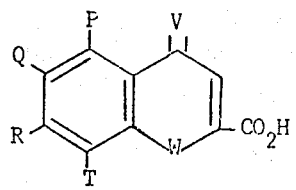

in which

P, Q, R, and T, which may be the same or different, each represent hydrogen, an alkyl, hydroxy, alkoxy, hydroxyalkoxy, alkoxyalkoxy, acetoxy, carboxy, amino, alkylamino, dialkylamino, alkenyl, p-toluenesulphonyloxy, aralkyl, phenyl, nitro, carboxy ester, alkenyloxy or acyl group, none of which groups contain more than 10 carbon atoms or an adjacent pair of P, Q, R and T, together with the adjacent carbon atoms in the benzene ring may form a fused 5 or 6 membered carbocyclic or oxygen containing heterocyclic ring, V and W, which are different, each represent oxygen or sulphur, provided that,
  i. not all of P, Q, R and T are hydrogen,
  ii. when T is a methoxy group, Q and R are hydrogen, V is oxygen and W is sulphur, P is not a methyl group, and pharmaceutically acceptable salts thereof.

According to our invention we also provide processes for the production of a compound of formula I, or a pharmaceutically acceptable salt therefore, which comprise a. producing a compound of formula Ia,

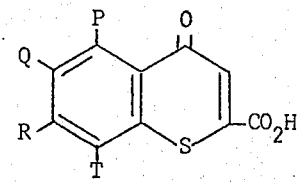

in which P, Q, R, T and the provisos are as defined above, by cyclising a compound of formula II,

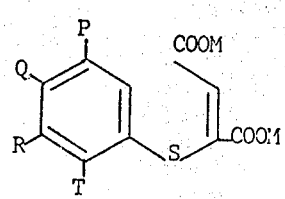

in which P, Q, R, T and the provisos are as defined above, and M represents hydrogen or an alkali metal cation, b. producing a compound of formula Ib,

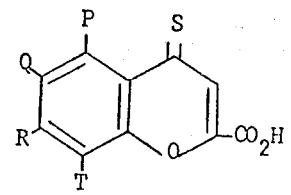

in which P, Q, R, T and the provisos are as defined above, by treating a corresponding compound of formula III,

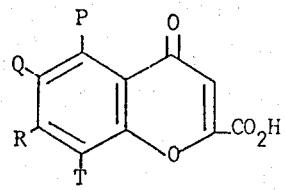

or of formula IV,

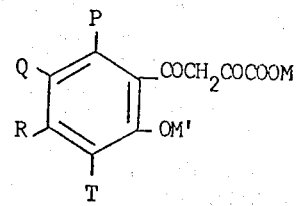

in which formulae III and IV P, Q, R, T, M and provisos are as defined above, and M' represents hydrogen, an alkali metal cation or an alkyl group, with phosphorous pentasulphide, or c. hydrolysing an ester of a compound of formula I, and where desired converting the compound of formula I produced to a pharmaceutically acceptable salt thereof.

The cyclisation of process (a) may be carried out by treating the compound of formula II with a cyclisation agent at ambient temperature or above. Suitable cyclisation agents include dehydrating agents, e.g. phosphorus pentoxide, polyphosphoric acids, sulphuric acid, chlorosulphonic acid and other Lewis acids. In certain cases it is also possible to use glacial acetic acid containing a small amount of hydrochloric or hydrobromic acid as cyclisation agent. When a dehydrating agent is used the reaction is preferably carried out under anhydrous conditions and it is preferred to subject the compound of formula II to a drying step before use.

Alternatively process (a) may be carried out by converting the —COOM groups of formula II to acyl chloride groups, e.g. by treatment with $PCl_3$, $PCl_5$ or $SOCl_2$ and subjecting the resulting acyl chloride to an intramolecular Friedel Crafts reaction.

Process (b) may be carried out in a solvent which is inert under the reaction conditions, e.g. benzene. The reaction is conveniently carried out at an elevated temperature, e.g. the reflux temperature of the reaction mixture. When the reaction product of process (b) is an ester this ester may be converted to the free acid by controlled alkaline hydrolysis.

Process (c) may be carried out using conventional techniques, e.g. controlled alkaline hydrolysis.

A number of other techniques such as those illustrated in the Examples may be used to produce compounds according to the invention.

The compounds of formula II may be made by reaction of a compound of formula V,

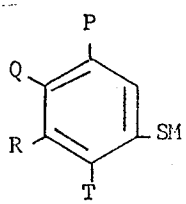

in which P, Q, R, T, M and the provisos are as defined above, with acetylene dicarboxylic acid, or an ester, or salt thereof, under alkaline conditions, to produce a product which is either the desired product or may be hydrolysed to yield the desired product. Where an ester is used an ester derived from a Cl to 10, or desirably from a Cl to 4, alcohol is preferred. The alkaline conditions may be provided by an organic base, e.g. benzyl trimethyl ammonium hydroxide, by an alkali metal hydroxide, or conveniently by using an alkali metal salt, e.g. a sodium salt, of formula V. The acetylene dicarboxylic acid, or the salt thereof and the compound of formula V are preferably reacted in approximately stoichiometric amounts using excess alkali in aqueous solution. The reaction is preferably carried out at from about 50° to 150°C.

In the above reaction the acetylene dicarboxylate ester may be replaced by an ester of a mono-halofumaric acid, or a precursor thereof. In this case the reaction is a condensation and involves the elimination of halogen acid or alkali metal halide between the halofumarate and the compound of formula V. The reaction is therefore preferably carried out in the presence of an acid binding agent when M represents H, though other methods of eliminating the halogen acid may be used if desired. It is also possible to use a precursor of the halofumarate ester, e.g. a halomaleate or a dihalosuccinate ester. When precursors are used it may be necessary to provide extra alkali to ensure conversion of the precursor to the desired halofumarate ester.

The compounds of formulae III and IV are either known, or may be made by methods analogous to the methods known for the manufacture of the known compounds.

The compounds of formula I and the intermediates therefor may be recovered and purified by techniques conventional in the recovery and purification of similar known compounds.

The processes outlined above may produce the free acids of formula I or may yield derivatives thereof. It is also within the scope of the present invention to treat the product of any of the above processes, after any isolation and purification steps that may be desired, in order to liberate the free acid therefrom or to convert one form of derivative into another. The methods used to isolate and purify any product may be those conventionally used. Thus, salts may be prepared by the use of alkaline conditions during the recovery and purification of the compound. Alternatively, the free acid may be obtained and subsequently converted to a desired salt by neutralisation with an appropriate base, e.g. an organic amine, or any alkali such as an alkali-metal or alkaline-earth metal hydroxide, carbonate or bicarbonate, preferably a mild base or alkali such as sodium carbonate or bicarbonate. Where the compound is recovered in the form of a salt, this salt may be converted to a more desirable salt, for example by a metathetical process. The esters may be formed by the reaction of an appropriate alcohol, alkyl sulphate or halocompound with free carboxyl groups in the compound of formula I; or may be formed by the reaction of an appropriate alcohol with an acyl halide of the compound of formula I. Alternatively, transesterification techniques may be used to exchange one ester group for another. The amides may be readily obtained, for example, by dehydration of the ammonium salt or by reaction of an ester or acyl halide with an appropriate amino compound such as ammonium hydroxide or a primary or secondary amine or an amino acid. Alternatively, the free acid of formula I may be condensed with an alkyl haloformate (e.g. chloroformate) in the presence of an organic base such as triethylamine, to yield a mixed anhydride which is then treated with an aminoacid or ester thereof in the presence of a suitable solvent to give an N-carboxyalkyl substituted amide. The mixed anhydride need not be isolated from the reaction mixture in which it was prepared, but may be treated in situ.

According to our invention we also provide a pharmaceutical composition comprising a compound of formula Ic,

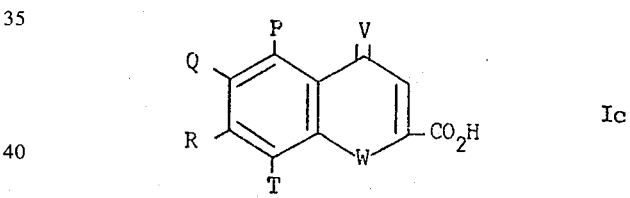

in which P, Q, R, T, V and W are defined in connection with formula I, save that there are no provisos, or a pharmaceutically acceptable salt, ester or amide thereof, in combination with a pharmaceutically acceptable diluent or carrier.

Pharmaceutically acceptable salts, (notably water soluble salts) include ammonium salts, alkali metal salts (e.g. sodium, potassium and lithium salts), alkaline earth metal salts (e.g. magnesium and calcium salts); and salts with organic bases, e.g. amine salts derived from mono, di-, or tri-lower alkyl or lower alkanolamines, (e.g. triethanolamine or triethylamine) and salts with heterocyclic amines such as piperidine or pyridine.

Preferred pharmaceutically acceptable salts of the compounds of formula Ic are the sodium and ammonium salts.

Pharmaceutically acceptable esters which may be mentioned include simple alkyl esters derived from alcohols containing from 1 to 10 carbon atoms (e.g. a methyl, ethyl, proply, or pentyl ester).

Pharmaceutically acceptable amides which may be mentioned include simple amides derived from ammonia or primary or secondary aliphatic or aromatic amines, such as mono- or di-lower (i.e. $C_1$ to 6) alkyl amines (for example diethylamine,) aniline or a monoalkylaniline e.g. methyl aniline.

The new compounds of formula I, pharmaceutically acceptable salts, esters and amides thereof and the new compositions of the invention are useful because they have pharmacological properties. In particular they inhibit the release of pharmacological mediators which arise from the combination of certain types of antibody and specific antigen, e.g. the combination of reaginic antibody with specific antigen. Both subjective and objective changes which result from the inhalation of specific antigen by sensitised subjects may be markedly inhibited by administration of the new compounds and compositions. Thus, the new compounds and compositions are useful in the treatment of 'extrinsic' allergic asthma. The new compounds and compositions are also of value in the treatment of so-called 'intrinsic' asthma (in which no sensitivity to extrinsic antigen can be demonstrated) and in the treatment of other conditions in which antigen-antibody reactions are responsible for disease, for example, hay fever, urticaria and auto-immune diseases.

For the sake of simplicity the pharmaceutical compositions will be described with respect to the compounds of formula Ic only, but pharmaceutically acceptable salts, esters and amides thereof are to be understood to be included.

The nature of the composition and the pharmaceutically acceptable carrier or diluent will, of course, depend upon the desired mode of administration, which may be for example, orally, by inhalation, parenterally, or by topical application.

The composition may be formulated in the conventional manner with the customary ingredients. For example, the compositions may be put up as aqueous solutions or suspensions, as powders or in tablet, cream, lotion or syrup form.

The compositions of the invention generally comprise a minor proportion of the compound of formula Ic and a major proportion of carrier or diluent. Thus, for example, aqueous solutions for administration by means of a conventional nebulizer may contain up to about 10% by weight of the active ingredient in sterile water; and compositions for dispensing from a pressurised container containing suspensions or solutions in liquified propellents may contain, for example, about 0.2–5% by weight of the active ingredient.

Compositions suitable for administration by inhalation comprise a compound of formula Ic, preferably in the form of a salt, e.g. the sodium salt, dissolved or suspended in water. Such compositions may be applied by means of a conventional nebulizer. However, the administration of the compounds of formula Ic by means of a conventional aerosol dispenser, is an alternative to nebulizer administration. Typical propellants suitable for use in the aerosol are those disclosed in U.S. Pat. No. 2868691 and sold under the trade name of Freon. The propellant should of course be of low toxicity, especially where the composition is to be ingested, e.g. inhaled, by the user. Where the compound of formula Ic is not soluble in the propellant, it may be necessary to add a surface-active agent to the composition in order to suspend the compound of formula Ic in the propellant medium, and such surface-active agents may be any of those commonly used for a similar purpose. The use of surface-active agents in similar compositions is more fully described in British Pat. Specification No. 1,063,512.

The compositions of the invention may also be administered in the form of powders by means of an insufflator device, e.g. that described in British Pat. Specification No. 1,122,284. In order to improve the properties of the powder, it may be desired to modify the surface characteristics of the powder particles, for example, by coating them with a pharmaceutically acceptable material such as sodium stearate. In addition, fine particle sized powders of the active ingredients may be mixed with a coarser diluent material, such as lactose, which may be present in a smaller, equal, or greater amount than the active ingredients, for example in from 50 to 150% by weight of the compound of formula Ic and such other active ingredients as may be present.

Whilst the inhalation of medicament has been described above with particular reference to oral administration, it will be appreciated that it may be desirable to administer the medicament nasally. The term inhalation is therefore used herein to denote, where the context permits, trachial administration by both oral and nasal routes.

The composition of the invention may also be administered as tablets, syrups and the like or by intradermal or intravenous injection in the conventional manner or as creams, lotions or pastes for use in dermatological treatments.

In addition to the compound of formula Ic and the ingredients required to present the compound in a form suitable for the selected mode of administration, other active ingredients may be present in the composition of the invention. Thus, in compositions for administration by inhalation, it may be beneficial to include a bronchodilator. Any bronchodilator may, within reason, be used. Suitable bronchodilators include isoprenaline, adrenaline, orciprenaline, isoetharine and pharmaceutically acceptable derivatives thereof, particularly the salts thereof. The use of isoprenaline sulphate is preferred. The amount of bronchodilator used will vary over a broad range, depending inter alia, upon the nature and activity of the bronchodilator and the compound of formula Ic used. However, the use of a minor proportion (i.e. less than 50% by weight based on the compound of formula Ic) of the bronchodilator is preferred. The use of from 0.1 to 10% by weight of the bronchodilator based on the weight of the compound of formula Ic is particularly preferred.

When used in inhibiting the effects of antibody-antigen reactions the compound or composition of the invention is administered to the site of the antibody-antigen reaction in the desired amount. The treatment may be one which requires repeated dosages of the medicament at regular intervals. The amount and freqency of medicament administered will depend upon many factors and no concise dosage rate or regimen can be generally stated. However, as a general guide, where the compounds are administered by inhalation to a patient suffering from acute allergic asthma, useful results may be achieved when the compounds are administered at a dosage of 0.1 to 50 mgs. Where the compounds are administered by the oral route, larger dosages may be given.

It will be appreciated that certain of the above values of P, Q, R and T may include groups which could be detrimentally affected by the reactants or reaction conditions used in the production of the compounds of formula I. In such cases the susceptible group may be blocked or shielded by conventional techniques during all or part of the production of the compounds of formula I.

Preferred compounds of formula I are those in which P, Q, R and T each represent hydrogen, an alkyl group containing from 1 to 6 carbon atoms, a hydroxy group, an alkoxy group containing from 1 to 10, and preferably from 1 to 5 carbon atoms, a hydroxy alkoxy group containing from 1 to 6 carbon atoms, an alkoxy alkoxy group containing from 1 to 6 carbon atoms, a carboxy group, an amino group, an alkyl amino group containing 2 or 3 carbon atoms, a dialkylamino group containing 2 to 4 carbon atoms, an alkenyl group containing from 1 to 6 carbon atoms, a phenylalkyl group containing from 7 to 10 carbon atoms e.g. a benzyl or phenethyl group, a phenyl group, a nitro group, a carboxy ester (e.g. derived from an alkanol) group containing from 1 to 6 carbon atoms, an alkenyloxy group containing from 1 to 6 carbon atoms, or an acyl, e.g. alkanoyl, group containing from 1 to 10, or preferably from 1 to 6 carbon atoms, or an adjacent pair of P, Q, R and T form the chains —$(CH_2)_4$—, —$(CH_2)_3$—, —O—$(CH_2)_3$—, —O$(CH_2)_2$—O—, —$CH_2$—$CH(CH_3)$—O—, —CH=CH—O—, —CH=$C(CH_3)$—O—, —O—CO—CH=$C(CH_3)$—, —CH=CH—CH=CH— or —O—$CH_2$—O—. These chains may be bonded to the thiachromone or thionchromone nucleus in either sense.

A further group of compounds comprise those of formula Ia in which P, Q, R and T, which may be the same or different, are hydrogen, an alkyl, hydroxy, alkoxy, hydroxyalkoxy, alkoxy-alkoxy, amino, alkylamino, dialkylamino, alkenyl, p-toluenesulphonyloxy, phenylalkyl, phenyl, nitro, carboxy ester, or alkenyloxy group none of which groups contain more than 10 carbon atoms.

A still further group of compounds are those of formula Ia in which P, Q, R and T, which may be the same or different, are hydrogen, hydroxyalkoxy, alkoxyalkoxy, alkoxy, phenyl, alkyl, nitro, hydroxy, p-toluenesulphonyloxy or alkenyloxy none of which groups contain more than 10 carbon atoms.

Particularly preferred compounds are those in which P, Q, R and T represent hydrogen, methoxy, ethoxy, phenyl, allyloxy, isoamyloxy, methyl, propyl, t-butyl, p-toluenesulphonyloxy, nitro or an adjacent pair of P, Q, R and T form a —$(CH_2)_4$—chain.

Specific compounds which may be mentioned are 6-(2-hydroxypropoxy)-1-thiachromone-2-carboxylic acid and 6-(2-ethoxyethoxy)-1-thiachrome-2-carboxylic acid.

The invention is illustrated, but in no way limited by the folliong Examples in which the parts are by weight.

EXAMPLE 1

6-Ethoxy-1-thiachromone-2-carboxylic acid a. 4-Ethoxyphenylthiofumaric acid

A solution of 15.4 parts of 4-ethoxythiophenol in 40 parts of water containing 16.8 parts of potassium hydroxide was prepared. To this solution was added a slurry of 20.9 parts of acetylene dicarboxylic acid monopotassium salt in 80 parts of water, and the mixture was well shaken and heated on the steam bath for 40 minutes. After cooling it was acidified with concentrated hydrochloric acid and the precipitated solid was filtered off, washed with a little water and crystallised twice from water to give 10.1 parts of 4-ethoxyphenylthiofumaric acid, melting point 159°–161°C (decomp.)

Analysis: H,
Found: C, 53.8; H,4.28; S, 12.0. $C_{12}H_{12}O_5S$ requires: C, 53.75; H, 4.48; S, 12.0%.

b. 6-Ethoxy-1-thiachromone-2-carboxylic acid

To 23 parts of concentrated sulphuric acid was slowly added 6.6 parts of 4-ethoxyphenylthio fumaric acid with stirring. After standing for 1 hour, the solution was poured on to 33 parts of ice and the greenish solid was filtered off, washed with water until acid-free and dried. the crude solid was crystallized from ethanol twice to give 2.2 parts of 6-ethoxy-1-thiachromone-2-carboxylic acid melting point 210°–211°C (decomp.).
Analysis:
Found: C, 57.8; H, 3.99; S, 13.1. $C_{12}H_{10}O_4S$ requires: C, 57.6; H, 4.03; S, 12.8%.

c. Sodium 6-Ethoxy-1-thiachromone-2-carboxylate

To part of 6-ethoxy-1thiachromone-2-carboxylic acid in water was added 0.336 parts of sodium bicarbonate. The mixture was stirred for several minutes and the resulting solution was filtered and freeze-dried to give sodium 6-ethoxy-1-thiachromone-2-carboxylate.

EXAMPLE 2

5,8-Dimethoxy-1-thiachromone-2-carboxylic acid a. 2,5-Dimethoxyphenylthio fumaric acid To a solution of 17 parts of potassium hydroxide in 40 parts of water was added 20 parts of 2,5-dimethoxythiophenol, followed by a suspension of 25 parts of acetylene dicarboxylic acid monopotassium salt in 100 parts of water. The mixture was heated on a steam-bath for 40 minutes then it was cooled and acidified with concentrated hydrochloric acid to give a precipitate which was filtered off and recrystallised from water to give 17.5 parts of 2,5-dimethoxyphenylthio fumaric acid melting point 183°–185°C.
Analysis: Found: C,51.1; H, 4.34%. $C_{12}H_{12}O_6S$ requires: C, 50.7; H, 4.26%.

b. 5,8-Dimethoxy-1-thiachromone-2-carboxylic acid

To 45 parts of concentrated sulphuric acid was added in small portions 12.5 parts of 2,5-dimethoxyphenylthio fumaric acid and the mixture was kept at room temperature for 30 minutes. The mixture was then poured on to 80 parts of ice and the resulting precipitate was filtered off and recrystallised from an acetone-alcohol mixture to give 3.5 parts of 5,8-dimethoxy-1-thiachromone-2-carboxylic acid melting point 210°–212°C.
Analysis: Found: c, 53.9; H, 3.8%. $C_{12}H_{10}O_5S$ requires: C, 54.14; H, 3.8%.

c. Sodium 5,8-dimethoxy-1-thiachromone-2-carboxylate

The sodium salt of the chromone acid was prepared by treatment with sodium bicarbonate and was freeze-dried as in Example 1.

EXAMPLE 3

5,8-Diethoxy-1-thiachromone-2-carboxylic acid a. 2,5-Diethoxyphenylthio fumaric acid 2,5-Diethoxythiophenol (12.7 parts) was dissolved in a solution of 9 parts of potassium hydroxide in 30 parts of water and to this solution a suspension of 13 parts of acetylene dicarboxylic acid mono-potassium salt in 50 parts of water was added. The mixture was heated on a steam-bath for 40 minutes then it was cooled and acidified with concentrated hydrochloric acid. A precipitate was obtained which was filtered off, washed with water and dried to give 17 parts of 2,5-diethoxyphenylthio fumaric acid melting point 135°–140°C.

b. 5,8-Diethoxy-1-thiachromone-2-carboxylic acid 2,5-Diethoxyphenylthio fumaric acid (8 parts) was added in small lots to a stirred solution of 42 parts of concentrated sulphuric acid and the resulting solution was allowed to stand for 30 minutes. The mixture was tipped onto 60 parts of ice and the precipitate was filtered off, washed with water and recrystallised from aqueous ethanol to give 4.3 parts of 5,8-diethoxy-1-thiachromone-2-carboxylic acid monohydrate melting point 182°C.

Analysis: Found: C, 53.6; H, 5.39% $C_{14}H_{14}O_5S H_2O$ requires: C, 53.84; H, 5.16%.

c. Sodium 5,8-Diethoxy-1-thiachromone-2-carboxylate

The sodium salt of the chromone was prepared by treatment with sodium bicarbonate and was freeze-dried as in Example 1.

EXAMPLE 4

5,6-Benzo-1-thiachromone-2-carboxylic acid a. 2-Naphthylthio fumaric acid

2-Naphthiol (5parts) was stirred with a solution of 5 parts of potassium hydroxide in 90 parts of water. The mixture was heated on a steam-bath and to it was added a suspension of 6 parts of acetylene dicarboxylic acid mono-potassium salt in 50 parts of water. The mixture was stirred and heated on a steam-bath for 50 minutes then it was filtered and the filtrate was cooled and acidified with concentrated hydrochloric acid. A precipitate was obtained which was filtered off, washed with water and dried to give 6.2 parts of 2-naphthylthio fumaric acid mono-hydrate, melting point 188°–193°C.

Analysis: Found: C, 57.7; H, 4.44%. $C_{14}H_{12}O_5S$ requires: C, 57.5; H, 4.52%.

b. 5:6 Benzo-1-thiachromone-2-carboxylic acid 2-naphthylthio fumaric acid (4 parts) was added in small lots to 18 parts of stirred concentrated sulphuric acid. The mixture was allowed to stand for 30 minutes then it was poured onto 50 parts of ice and the resulting precipitate was filtered off, washed with water and recrystallised from alcohol to give 1.1 parts of 5:6 benzo-1-thiachromone-2-carboxylic acid melting point 238°–239°C.

Analysis: Found: C, 65.4; H, 3.12; S, 12.3%. $C_{14}H_8O_3S$ requires: C, 65.63; H, 3.15; S, 12.5%.

The sodium salt of the chromone was prepared by treatment with sodium bicarbonate and was freeze-dried as in Example 1.

EXAMPLE 5

Cyclohexano-(g)-4-thionchromone-2-carboxylic acid [Process (b)]

a. Ethyl cyclohexano-(g)-4-thionchromone-2-carboxylate

A mixture of 5.8 parts of ethyl (3-hydroxy-5,6,7,8-tetrahydro-2-naphthoyl) pyruvate, 8.88 parts of phosphorus pentasulphide and 80 parts of benzene were heated under reflux with stirring for 5 hours. The benzene was removed by distillation and the remaining solid was dissolved in petrol with warming, chromatographed on a silica column and eluted with petrol (b. pt., 60°–80°C) and ethyl acetate in a ratio of 3 parts to 1 part respectively.

The first colourless solutions which came from the column yielded 0.5 parts of starting material.

The main green band was eluted and after removal of the solvent the solid was crystallised from petrol (60°–80°) with charcoaling to give 1.95 parts of ethyl cyclohexano-(g)-4-thionchromone-2-carboxylate, m.pt., = 97.5°–99.5°C.

Analysis: Found: C, 66.5; H, 5.26; S, 11.4%. $C_{16}H_{16}O_3S$ requires: C, 66.65; H, 5.59; S, 11.1%.

b. Cyclohexano-(g)-4-thionchromone-2-carboxylic acid

To a warm solution of 0.341 parts of ethyl cyclohexano-(g)-4-thionchromone-2-carboxylate in 15 parts of methanol was added 1.22 parts by volume of a 0.96N solution of sodium hydroxide in methanol. After heating under reflux for 1 hour, 30 parts of water were added and the methanol was removed by distillation. The aqueous solution was cooled, diluted and acidified to give a pale green precipitate which was filtered off, washed with water and dried.

The crude product (0.31 parts) was crystallised from aqueous ethanol to give needles of cyclohexano-(g)-4-thionchromone-2-carboxylic acid, m.p. 215°–219°λ (decomp.).

Analysis: Found: C, 64.6; H, 4.55; S, 11.8%. $C_{14}H_{12}O_3S$ requires: C, 64.6; H, 4.65; S, 12.3%.

c. Sodium Cyclohexano-(g)-4-thionchromone-2-carboxylate

A portion of the cyclohexano-(g)-4-thionchromone-2-carboxylic acid was dissolved by warming gently in water with the equivalent amount of sodium bicarbonate, and the solution was freeze-dried to give sodium cyclohexano-(g)-4-thionchromone-2-carboxylate.

EXAMPLE 6

6-Phenyl-1-thiachromone-2-carboxylic acid a. 4-Biphenylyltiofumaric acid

A solution of 7.7 parts of 4-mercaptobiphenyl in 36 parts of water containing 5.1 parts of potassium hydroxide was prepared. To this solution was added 7.0 parts of acetylenedicarboxylic acid monopotassium salt and the mixture was well-shaken and heated on a steam bath for 90 minutes. The mixtures was then filtered whilst hot, the solution was acidified with dilute hydrochloric acid and the precipitated solid was filtered off. The product was dried to leave 8.5 parts of a yellow solid, which was crystallised from aqueous acetic acid to give 4.7 parts of 4-biphenylyltiofumaric acid, melting point 213°–5°C.

b. 6-Phenyl-1-thiachromone-2-carboxylic acid

A slurry was prepared of 11.0 parts of 4-biphenylythio fumaric acid with 170 parts of polyphosphoric acid and heated at 100°–110°C for 6 hours. The mixture was then stirred with 500 parts of icewater and the precipitated solid was filtered off, washed with water and crystallised twice from aqueous dioxan to give 2.3 parts of 6-phenyl-1-thiachromone-2-carboxylic acid, melting point 220°C.

Analysis: Found: C, 68.2; H, 3.5; S, 11.1. $C_{16}H_{10}O_3S$ requires: C, 68.1; H, 3.6; S, 11.3.

c. Sodium 6-phenyl-1-thiachromone-2-carboxylate

The sodium salt of the chromone acid was prepared by treatment with sodium bicarbonate and was freeze-dried as in Example 1.

EXAMPLE 7

6-Methyl-1-thiachromone-2-carboxylic acid 4.7 parts of 4-methylphenylthio fumaric acid, made in analogous manner to part (a) of Example 1, was added in small lots to 20 parts of stirred concentrated sulphuric acid. The solution was allowed to stand for 30 minutes and then it was cautiously poured on to ice. The resulting precipitate was filtered off, washed with water and crystallised from an ethanol/dioxan mixture to give 2.3 parts of 6-methyl-1-thiachromone-2-carboxylic acid, melting point 236°–7°C.

Analysis: Found: C, 60.5; H, 3.78; S, 14.2. $C_{11}H_8O_3S$ requires: C, 60.0; H, 3.66; S, 14.53%.

The sodium salt of 6methyl-1-thiachromone-2-carboxylic acid was prepared by neutralisation with sodium bicarbonate and freeze-drying the solution.

EXAMPLE 8

6-Nitro-1-thiachromone-2-carboxylic acid a. 4-Nitrophenylthiofumaric acid

To a solution of 6 parts of potassium hydroxide in 100 parts of water was added 8 parts of 4-nitrothiophenol. The resulting solution was filtered and the filtrate and treated with a slurry of 8 parts of acetylenedicarboxylic acid monopotassium salt in 20 parts of water. The mixture was heated on a steam bath for 30 minutes, cooled, treated with animal charcoal and filtered through a filter aid such as 'hyflo' and finally it was acidified with 5N hydrochloric acid. The precipitated solid was filtered off washed with water and dried to leave 10.1 parts of 4-nitrophenylthiofumaric acid, melting point 168°–76°C.

Analysis: Found: C, 44.1; H, 2.51; N, 5.22; S, 12.59. $C_{10}H_7NO_6S$ requires: C, 44.6; H, 2.62; N, 5.21; S, 11.89%.

b. 6-Nitro-1-thiachromone-2-carboxylic acid

To 22 parts of chlorosulphonic acid was added, in small lots, 3.0 parts of 4-nitrophenylthiofumaric acid. The solution was swirled and was then left to stand for 5 minutes. The solution was carefully diluted with 25 parts of concentrated sulphuric acid and swirled until no more gas was evolved, heated briefly at 50°C, cooled and poured on to 200 parts of ice. The precipitate was filtered off washed with water and crystallised from aqueous ethanol and finally dried in vacuo to give 2.0 parts of 6-nitro-1-thiachromone-2-carboxylic acid, melting point 220°C.

Analysis: Found: C, 48.3; H, 2.06; N, 5.52. $C_{10}H_5NO_5S$ requies: C, 47.8; H, 1.99; N, 5.57%.

c. Sodium 6-nitro-1-thiachromone-2-carboxylate

The sodium salt of the chromone acid was prepared by treatment with sodium bicarbonate and freeze-dried ad in Example 1.

EXAMPLE 9

1-Thiachromone-2,8-dicarboxylic acid a. 2-Carboxyphenylthiofumaric acid

To a solution of 2.0 parts of sodium hydroxide, 8.5 parts of sodium bicarbonate and 7.7 parts of 2-mercaptobenzoic acid in 100 parts of water was added 7.7 parts of acetylenedicarboxylic acid monopotassium salt. The resulting solution was heated on a steam bath for 40 minutes, cooled and acidified with concentrated hydrochloric acid. The mixture was warmed to coagulate the precipitate which was then filtered off washed with water and dried to leave 11.2 parts of 2-carboxyphenylthiofumaric acid, melting point, 194°–8°C.

Analysis: Found: C, 48.7; H, 3.01; S, 12.22. $C_{11}H_8O_6S$ requires: C, 49.3; H, 2.99; S, 11.94%.

b. 1-Thiachromone-2,8-dicarboxylic acid

To 28 parts of chlorosulphuric acid was added in small lots 3 parts of 2-carboxyphenylthiofumaric acid. The solution was swirled, and allowed to stand for 5 minutes. It was then diluted with 30 parts of concentrated sulphuric acid, swirled until no more gas was evolved and heated briefly at 50°C. Finally the solution was carefully poured on to 250 parts of ice. The precipitated material was filtered off, washed with water, crystallised from aqueous ethanol and dried in vacuo to leave 1.8 parts of 1-thiachromone-2,8-dicarboxylic acid hemi-hydrate, melting point 340°C (decomposition).

Analysis Found: C, 51.0; H, 2.66; S, 12.25. $C_{11}H_6O_5S.0.5H_2O$ requires: C, 51.0; H, 2.71; S, 12.36.

c. Disodium -thiachromone-2,8-dicarboxylate

The disodium salt of the chromone dicarboxylic acid was prepared by treatment with sodium bicarbonate and freeze-dried as in Example 1.

EXAMPLE 10

6-Hydroxy-1-thiachromone-2-carboxylic acid a. 4-Hydroxyphenylthiofumaric acid

To a solution of 45 parts of potassium hydroxide and 25.2 parts of monothiohydroquinone in 300 parts of water was added 31 parts of acetylenedicarboxylic acid monopotassium salt. The mixture was heated on a steam bath for 1 hour, then it was cooled, filtered and acidified with concentrated hydrochloric acid. The resulting precipitate was filtered off, washed with water and dried to leave 31.7 parts of 4-hydroxyphenylthiofumaric acid, melting point 199.5°–201°C.

Analysis: Found: C, 49.7; H, 3.47; S, 13.6. $C_{10}H_8O_5S$ requires: C, 50.0; H, 3.33; S, 13.34%.

b. 6-Hydroxy-1-thiachromone-2-carboxylic acid

To a stirred solution of 143 parts of chlorosulphonic acid was added, in small lots over a 25 minute period, 30 parts of 4-hydroxyphenylthiofumaric acid. The solution was stirred for 10 minutes heated briefly at 50°C, cooled and cautiously poured on to 1000 parts of ice. The resulting precipitate was filtered off, washed with water and crystallised from 90% aqueous dioxan to give 20.2 parts of 6-hydroxy-1-thiachromone-2-carboxylic acid, melting point 251°C (decomposition).

Analysis: Found: S, 14.5. $C_{10}H_6O_4S$ requires: S, 14.4%.

c. Sodium 6-hydroxy-1-thiachromone-2-carboxylate

The sodium salt of the chromone acid was prepared by treatment with sodium bicarbonate and freeze-dried as in Example 1.

EXAMPLE 11

6-Allyloxy-1-thiachromone-2-carboxylic acid a. Ethyl 6-hydroxy-1-thiachromone-2-carboxylate A solution of 10.6 parts of 6-hydroxy-1-thiachromone-2-carboxylic acid and 9 parts of concentrated sulphuric acid in 750 parts of ethanol was heated under reflux for 20 hours. Most of the ethanol was evaporated off and the residual solution was diluted with 500 parts of water, which caused precipitation of a solid. The solid was filtered off, washed with dilute sodium bicarbonate solution and with water and was finally crystallised from ethanol to give 9.4 parts of ethyl 6-hydroxy-1-thiachromone-2-carboxylate, melting point 217°-8°C.

Analysis: Found: C, 57.6; H, 4.06; S, 12.82. $C_{12}H_{10}O_4S$ requires: C, 57.6; H, 4.00; S, 12.8%.

b. Ethyl 6-allyloxy-1-thiachromone-2-carboxylate

A mixture of 12.5 parts of ethyl 6-hydroxy-1-thiachromone-2-carboxylate, 6.8 parts of allyl bromide and 9.7 parts of anhydrous potassium carbonate in 80 parts of acetone was heated under reflux for 20 hours. The mixture was filtered and the solution was evaporated. The residual material was dissolved in chloroform and the solution was washed with water, then the chloroform was evaporated and the remaining material was crystallised from ethanol to give 11.8 parts of ethyl 6-allyloxy-1-thiachromone-2-carboxylate, melting point, 107.5°-8°C.

Analysis: Found: C, 61.9; H, 4.86; S, 11.20. $C_{15}H_{14}O_4S$ requires: C, 62.1; H, 4.83; S, 11.04%.

c. 6-Allyloxy-1-thiachromone-2-carboxylic acid

A mixture of 3 parts of ethyl 6-allyloxy-1-thiachromone-2-carboxylate, 0.87 parts of sodium bicarbonate and 4 parts of methanol in 25 parts of water was heated under reflux for several minutes then the methanol was distilled. The aqueous solution was diluted with 25 parts of water, filtered and acidified with concentrated hydrochloric acid to give a precipitate which was filtered off, washed with water and dried to give 2.6 parts of 6-allyloxy-1-thiachromone-2-carboxylic acid, melting point, 200°-200.5°C.

Analysis: Found: C, 59.1; H, 3.94. $C_{13}H_{10}O_4S$ requires: C, 59.5; H, 3.82%.

d. Sodium 6-allyloxy-1-thiachromone-2-carboxylate

The sodium salt of the chromone acid was prepared by treatment with sodium bicarbonate and freeze dried as in Example 1.

EXAMPLE 12

6,8-Di-isopropyl-1-thiachromone-2-carboxylic acid, sodium salt

A mixture of 23 parts of 2,4-diisopropylbenzenethiol, 13.4 parts of potassium hydroxide and 18.3 parts of acetylene dicarboxylic acid, mono-potassium salt in 100 parts of water was stirred and heated on a steambath for 40 minutes. The mixture was then cooled, filtered and acidified with concentrated hydrochloric acid. A precipitate was obtained which was filtered off, washed with water and dried to leave 32 parts of 2,4-diisopropylphenylthiofumaric acid, melting point 186°-9°C.

To 280 parts of stirred chlorosulphonic acid surrounded by an ice/water bath was gradually added 30 parts of 2,4-diisopropylphenylthiofumaric acid over a 25 minute period. The mixture was then allowed to stand at room temperature for 30 minutes and was cautiously poured on to 700 parts of ice. A precipitate was obtained, which was filtered off, washed with water and crystallized from aqueous ethanol to give 15 parts of 6,8-di-isopropyl-1-thiachromone-2-carboxylic acid, melting point, 188°-190°C (decomp).

Analysis: Found: C, 65.12; H, 6.25; S, 11.19%. $C_{16}H_{18}O_3S$ requires: C, 66.2; H, 6.21; S, 11.04%.

A mixture of 14.3 parts of 6,8-di-isopropyl-1-thiachromone-2-carboxylic acid and 4.14 parts of sodium bicarbonate in 350 parts of water was prepared, filtered and freeze-dried to give 15 parts of 6,8-di-isopropyl-1-thiachromone-2-carboxylic acid, sodium salt.

EXAMPLE 13

6-(3-Methylbutoxy)-1-thiachromone-2-carboxylic acid, sodium salt

A mixture of 9 parts of ethyl 6-hydroxy-1-thiachromone-2-carboxylate, 15 parts of isoamyl bromide and 14 parts of anhydrous potassium carbonate in 130 parts of acetone was stirred and heated under reflux for 18 hours. Insoluble material was then filtered off and washed with acetone and the total acetone solution was evaporated to leave a yellow solid, which was crystallized from ethanol to give 4.1 parts of ethyl 6-(3-methylbutoxy)-1-thiachromone-2-carboxylate, melting point 83°-84°C. This entire product was heated under reflux for 2 hours with a solution of 1.5 parts of sodium bicarbonate in 35 parts of water and 25 parts of methanol. The methanol was then boiled off and the solution was diluted with 70 parts of water. The aqueous solution was thoroughly washed with ether, filtered then acidified with concentrated hydrochloric acid. A precipitate was obtained which was filtered off, washed with water and dried, then extracted with boiling benzene. The product was then filtered off and dried to leave 3.95 parts of 6-(3-methylbutoxy)-1-thiachromone-2-carboxylic acid, melting point 208°-209°C.

Analysis: Found: C, 61.54; H, 5.56%. $C_{15}H_{16}O_4S$ requires: C, 61.64; H, 5.52%.

A mixture of 3.5 parts of 6-(3-methylbutoxy)-1-thiachromone-2-carboxylic acid and 1.0 parts of sodium bicarbonate in 50 parts of water was heated, filtered and freeze-dried then further dried in a vacuum oven at 50°C for 2 hours to leave 3.6 parts of 6-(3-methylbutoxy)-1-thiachromone-2-carboxylic acid, sodium salt.

EXAMPLE 14

5-(3-Methylbutoxy)-8-propyl-1-thiachromone-2-carboxylic acid sodium salt a. 0-5-(3-Methylbutoxy)-2-propylphenyl N,N-dimethylthiocarbamate 24 Parts of a 50% dispersion of sodium hydride in mineral oil was added portionwise to an anhydrous solution of 111 parts of 5-(3-methylbutoxy)-2-propylphenol in 400 parts of dimethylformamide. After effervescence had ceased, the resulting clear solution was cooled to +10°C. 83 parts of N,N-dimethylthiocarbamoyl chloride were added in one portion and the ice bath was removed. The temperature began to rise and was taken to 80° – 90°C for 1 hour and finally stirred at room temperature for 17 hours. The reaction mixture was poured into 2000 parts of water followed by extraction with 6 × 400 parts of benzene. The latter extract was washed with water, 5% aqueous sodium hydroxide, brine, dried over magnesium sulphate, filtered and evaporated to dryness to yield 153.5 parts of 0-5-(3-methylbutoxy)-2-propylphenyl N,N-dimethylthiocarbamate as a yellow oil.

Spectral Confirmation

The n.m.r. spectrum in carbon tetrachloride with tetramethylsilane as internal reference confirmed the structure of the product as 0-5-(3-methylbutoxy)-2-propylphenyl-N,N-dimethylthiocarbamate. The most prominent feature of the spectrum was the presence of two singlet resonances at 6.7τ and 6.8τ for the methyl groups attached to nitrogen, suggesting hindered rotation about the

bond.

b. S-5-(3-Methylbutoxy)-2-propylphenyl N,N-dimethylthiocarbamate 153.3 Parts of 0-5-(3-methylbutoxy)-2-propyl-N,N-dimethylthiocarbamate were heated at 295° – 300°C under nitrogen for 30 minutes and cooled. 136.1 Parts of S-5-(3-methylbutoxy)-2-propylphenyl N,N-dimethylthiocarbamate were obtained as an oil.

Spectral Confirmation

The n.m.r. spectrum in carbon tetrachloride with tetramethylsilane as internal reference confirmed the structure of the product as S-5-(3-methylbutoxy)-2-propylphenyl N,N-dimethylthiocarbamate. The most prominent feature of the spectrum was the presence of a singlet resonance peak for the two N,N-dimethyl groups, suggesting that the

bond could rotate more freely than the

bond in the previous compound.

c. 5-(3-Methylbutoxy)-2-propylthiophenol

A solution of 136.1 parts of S-5-(3-methylbutoxy)-2-propylphenyl N,N-dimethylthiocarbamate and 280 parts of potassium hydroxide in 1000 parts of digol was stirred under nitrogen at 120° – 130° for 9 hours, after which no dimethylamine could be detected in the effluent nitrogen. The mixture was cooled, poured into 8000 parts of water and the resulting solution was acidified to pH 1 with hydrochloric acid. The mixture was extracted with ether and the latter was washed with water, dried over magnesium sulphate, filtered and evaporated to dryness to give 95.7g of the desired product 5-(3-methylbutoxy)-2-propylthiophenol.

Spectral Confirmation

The n.m.r. spectrum in carbon tetrachloride with tetramethylsilane as internal reference confirmed the structure of the product as 5-(3-methylbutoxy)-2-propylthiophenol. The most prominent feature of the spectrum was a sharp, singlet resonance at 6.98τ for free —SH, which was exchangeable with deuterium oxide.

d. [5-(3-Methylbutoxy)-2-propylphenylthio] fumaric acid

A solution of 95.7 parts of 5-(3-methylbutoxy)-2-propylthiophenol, 54 parts of potassium hydroxide and 73 parts of acetylene dicarboxylic acid mono potassium salt in 350 parts of water was refluxed for 40 minutes and cooled. The mixture was filtered through Whatman 54 filter paper to remove an oil residue and the filtrate was acidified to pH 1 with concentrated hydrochloric acid. The resulting yellow precipitate was collected, washed with water and dried in vacuo to give 67.8 parts of the desired product as a yellow powder, mp 121° – 129°C Crystallization from 15% ethanol-water afforded pure [5-(3-methylbutoxy)-2-propylphenylthio] fumaric acid, m.p. 131° – 133°C.

Spectral Confirmation

The molecular weight of 352 was cofirmed by mass spectroscopy. The n.m.r. spectrum in deuterochloroform displayed a sharp, singlet resonance for the ethylenic (vinylic) proton at 3.6τ and a broad 2H singlet resonance at 1.9 for the carboxylic acid protons, which were exchangeable with deuterium oxide.

e. 5-(3-Methylbutoxy)-8-propyl-1-thiachromone-2-carboxylic acid

65 Parts of [5-(3-methylbutoxy)-2-propylphenylthio] fumaric acid was added portionwise to 240 parts of chlorosulphonic acid over a period of 20 minutes with stirring. The dark, orange solution was allowed to stand for 10 minutes before pouring cautiously into 2000 parts of ice. The resulting solid precipitate was allowed to settle under the gravity. The solid was filtered off, washed with water and sucked dry. At this point the material, became oily and it was extracted into ethyl acetate. The latter was dried over magnesium sulphate, filtered, concentrated in vacuo and allowed to crystallize in the refrigerator. The resulting yellow crystalline solid was collected and dried in vacuo to afford 8.4 parts of the desired product, mp 153° – 154°C (d). Recrystallization from ethyl acetate gave 6.0 parts of 5-(3-methylbutoxy)-8-propyl-1-thiachromone-2-carboxylic acid, mp 156°C (d).

Analysis: Found: C,64.5; H,6.6%. Calculated for $C_{18}H_{22}O_4S$: C,64.6; H,6.6%.

Spectral Confirmation

The molecular weight of 334 was confirmed by mass spectroscopy.

The n.m.r. spectrum in hexadeutero-dimethylsulphoxide revealed the 3-proton as a sharp, singlet resonance at 2.7τ.

The infra red spectrum displayed peaks at 2500 cm$^{-1}$ for the H bonded carboxyl group and 1730 cm$^{-1}$ for the C=O str. of the carboxyl group.

f. 5-(3-methylbutoxy)-8-propyl-1-thiachromone-2-carboxylic acid sodium salt 5.9 Parts of 5-(3-methylbutoxy)-8-propyl-1-thiachromone-2-carboxylic acid was reacted with 1.83 parts of sodium bicarbonate in 50 parts of water. The resulting yellowish solution was freeze dried to give 5.7 parts of 5-(3-methylbutoxy)-8-propyl-1-thiachromone-2-carboxylic acid sodium salt.

Analysis: Found: C,57.7; H,6.2%. Calculated for $C_{18}H_{21}NaO_4S.H_2O$: C,57.7; H,6.2%.

Spectral Confirmation

The n.m.r. spectrum in hexadeuterio-dimethylsulphoxide revealed the 3-proton as a sharp singlet at 2.9τ.

EXAMPLE 15

5-(3-Methylbutoxy)-8-methyl-1-thiachromone-2-carboxylic acid a. 4-(3-Methylbutoxy)-2-nitrotoluene

A mixture of 50 parts of 3-nitro-p-cresol, 94 parts of isoamyl bromide and 94.2 parts of anhydrous potassium carbonate in 650 parts of acetone was stirred and heated under reflux for 18 hours. Insoluble material was filtered off and washed with acetone and the total acetone solution was evaporated. An oil remained which was partitioned between 250 parts of ether and 500 parts of water. The ethereal layer was isolated dried over anhydrous magnesium sulphate then evaporated to leave 66.6 parts of 4-(3-methylbutoxy)-2-nitrotoluene as a pale yellow oil.

Analysis: Found: C,63.88; H,7.59; N,6.17. $C_{12}H_{17}NO_3$ requires: C,64.55; H,7.68; N,6.27%.

b. 5-(3-Methylbutoxy)-2-methylaniline

A mixture of 30 parts of 4-(3-methylbutoxy)-2-nitrotoluene and 0.2 parts of 5% palladium on charcoal in 100 parts of ethanol was shaken and subjected to a hydrogen gas pressure of 3 atmospheres at 50°C for a period of 15 hours.

When ordinary atmospheric conditions had been restored the palladium/charcoal catalyst was filtered off and the ethanolic solution was evaporated to leave 24 parts of 5-(3-methylbutoxy)-2-methylaniline as an orange/red oil.

Characterization

A solution of 1 part of 5-(3-methylbutoxy)-2-methylaniline in 50 parts of ether was treated with anhydrous hydrogen chloride gas until no further precipitation occurred. The precipitate was filtered off and dried to leave 1.2 parts of 5-(3-methylbutoxy)-2-methylaniline hydrochloride as a grey powder.

Analysis: Found: C,63.06; H,8.52; N,5.79. $C_{12}H_{19}NO.HCl$ requires: C,62.80; H,8.71; N,6.10%.

c. 5-(3-Methylbutoxy)-2-methylbenzenethiol

A mixture of 24.1 parts of 5-(3-methylbutoxy)-2-methylaniline, 30 parts of concentrated hydrochloric acid, 60 parts of dioxan and 50 parts of water was cooled to −7°C stirred and treated dropwise over a 1 hour with a solution of 9.7 parts of sodium nitrite in 20 parts of water. The mixture was stirred for a further 1 hour at −7° to −0°C then it was added in portions to a stirred solution of 36 parts of ethyl potassium xanthate in 50 parts of water maintained at 40° - 43°C. This mixture was stirred for 1 hour then it was cooled and poured into 400 parts of ether. The etheral layer was isolated washed with water dried over anhydrous magnesium sulphate then evaporated to leave a red oil.

The red oil was dissolved in 100 parts of ethanol and the solution was stirred and treated with 34 parts of potassium hydroxide over a 25 minute period. The mixture was stirred and heated under reflux for 10 hours then it was diluted with 200 parts of water and acidified with 100 parts of 5 Normal sulphuric acid solution. The mixture was extracted with 100 parts of benzene and the benzene solution was treated with 50 parts of 2 Normal sulphuric acid solution and 6 parts of zinc powder. This mixture was heated under reflux on a steambath for 1 hour then the benzene solution was isolated, washed with water, filtered and evaporated to leave 21 parts of 5-(3-methylbutoxy)-2-methylbenzene thiol.

d. [5-(3-Methylbutoxy-2-methylphenylthio]fumaric acid

To a soluton of 12 parts of potassium hydroxide in 200 parts of water were added 21 parts of 5-(3 -methylbutoxy)-2-methylbenzenethiol. The mixture was heated on a steam-bath for 5 minutes, then to it was added 20 parts of acetylene dicarboxylic acid, mono potassium salt. The new mixture was swirled until it was homogeneous then it was heated on a steam bath for 40 minutes cooled, filtered three times through 'hyflo' to remove oily contaminants and then the clear aqueous solution was acidified with concentrated hydrochloric acid. A brown gummy precipitate was obtained which solidified on scratching. The solid was filtered off washed with water and dried to leave 11.4 parts of [5-(3-methylbutoxy)-2-methylphenylthio] fumaric acid hemi-hydrate, melting point 145° - 148°C.

Analysis: Found: C,57.35; H,5.99; S,9.22. $C_{16}H_{20}O_5S.½H_2O$ requires: C, 57.65; H, 6.31 S,9.61%.

e. 5-(3-Methylbutoxy)-8-methyl-1-thiachromone-2-carboxylic acid

To an ice-cooled solution of 45 parts of chlorosulphonic acid was added, in small lots over 10 minutes, 8 parts of [5-(3-methylbutoxy)-2-methylphenylthio] fumaric acid. The mixture was then allowed to stand for 20 minutes and was then cautiously poured on to 200 parts of ice. Precipitated material was filtered off, washed with water then dried in a vacuum at 45°C to leave a dark orange solid, which was extracted with 4 lots of 60 parts of hot ethyl acetate. The extract was filtered, then 130 parts of the ethyl acetate were evaporated off. On standing a solid crystallised from the concentrated solution. This solid was filtered off washed with a little ethyl acetate, dried and crushed to give 2.55 parts of 5-(3-methylbutoxy)-8-methyl-1-thiachromone-2-carboxylic acid, melting point 169°C (decomp).

Analysis: Found: C,62.54; H,5.95; S,11.17. $C_{16}H_{18}O_{5}S$ requires: C,62.74; H,5.92; S,10.45%.

f. 5-(3-Methylbutoxy)-8-methyl-1-thiachromone-2-carboxylic acid, sodium salt A solution of 3.7 parts of 5-(3-methylbutoxy)-8-methyl-1-thiachromone-2-carboxylic acid and 0.98 parts of sodium bicarbonate in 45 parts of water was prepared filtered and freeze-dried, then further dried in vacuo at 50°C for 1 hour to give 3.8 parts of 5-(3-methylbutoxy)-8-methyl-1-thiachromone-2-carboxylic acid, sodium salt.

EXAMPLE 16

The compounds shown in the following Table and their sodium salts were made by the method indicated in Example 1.

| Compound | m.p. °C. | Elemental Analysis Found | | |
|---|---|---|---|---|
| | | C | H | S |
| 6,8-Di-t-butyl-1-thiachromone-2-carboxylic acid | 201 (decomp) | 68.05 | 7.21 | 10.23 |
| 8-Methyl-5-isopropyl-1-thiachromone-2-carboxylic acid | 213–214 (decomp) | 64.33 | 5.34 | 11.8 |
| 6-t-Butyl-thiachromone-2-carboxylic acid | 204 (decomp) | 64.12 | 5.46 | 12.37 |

EXAMPLE 17

6-p-Toluenesulphonyloxy-1-thiachromone-2-carboxylic acid

To a solution of 8.9 parts of 6-hydroxy--thiachromone---thiachromonone-2-carboxylic acid and 3.2 parts of sodium hydroxide in 100 parts of water was added 8.0 parts of p-toluensulphonyl chloride and the mixture was heated on a steam-bath for 1 hour. The nixture was then diluted with 150 parts of water, re-heated and filtered while hot then acidified, while still warm, with dilute hydrochloric acid. A precipitate was formed, which was filtered off, washed with water and crystallized from aqueous ethanol. The product was dried, then recrystallized from a toluene/methanol mixture to give 7.2 parts of 6-p-toluenesulphonyloxy-1-thiachromone-2-carboxylic acid, melting point, 218°–219°C (decomp).

Analysis: Found: C,54.29; H,3.30; S,17.26. $C_{17}H_{12}O_{6}S_{2}$ requires: C,54.26; H,3.21; S,17.01%.

The 6-p-toluenesulphonyloxy-1-thiachromone-2-carboxylic acid was converted to its sodium salt by the method indicated in Example 12.

EXAMPLE A

The procedure set out below may be used to assess the effectiveness of a compound in inhibiting the release of the pharmacological mediators of anaphylaxis.

In this test, the effectiveness of the compounds in inhibiting the passive cutaneous anaphylactic reation in rats is assessed. It has been proved that this form of test gives reliable qualitative indications of the ability of the compounds under test to inhibit antibody-antigen reactions in man.

In this test method Charles River/Fisons bred rats (male and female) having a body weight of from 100 to 150 gms are infected subcutaneously at weekly intervals with N. brasiliensis larvae in doses increasing from about 2000 larvae per animal to 12000 larvae per animal in order to establish the infection. After 8 weeks the rats are bled by heart puncture and 15–20 mls. of blood collected from each animal. The blood samples are then centrifuged at 3500 rpm. for 30 minutes in order to remove the blood cells from the blood plasma. The serum is collected and used to provide a serum containing N. brasiliensis antibody. A pilot sensitivity test is carried out to determine the least quantity of serum required to give a skin weal in control animals in the test described below of 2 cm diameter. It has been found that optimum sensitivity of rats in the body weight range 100–130 gms is obtained using a serum diluted with eight parts of physiological saline solution. This diluted solution is called antibody serum A.

The antigen to react with the antibody in serum A is prepared by removing N. brasiliensis worms from the gut of the infested rats, centrifuging the homogenate and collecting the supernatent liquor. This liquor is diluted with saline to give a protein content of 1 mg/ml and is known as a solution B.

Charles River/Fisons bred rats in the body weight range 100 to 130 gms are sensitised by intradermal injection of 0.1 mls of solution A into the right flank. Sensitivity is allowed to develop for 24 hours and the rats are then injected intravenously with 1 ml/100 gms body weight of a mixture of solution B (0.25 mls), Evans Blue dye solution (0.25 mls) and the solution of the compound under test (0.5 mls varying percentages of active matter). Insoluble compounds are administered as a separate intraperitoneal injection 5 minutes before intravenous administration of solution B and Evans Blue dye. For each percentage level of active matter in the solution under test five rats are injected.

Five rats are used as controls in each test. The dosages of the compound under test are selected so as to give a range of inhibition values.

Thirty minutes after injection of solution B the rats are killed and the skins removed and reversed. The intensity of the anaphylactic reaction is assessed by comparing the size of the characteristic blue weal produced by spread of the Evans Blue dye form the sensitisation site, with the size of the weal in the control animals. The size of the weal is rated as 0 (no weal detected, i.e. 100% inhibition) to 4 (no difference in size of weal i.e. no inhibition) ad the percentage inhibition for each dose level calculated as:

$$\% \text{ inhibition} = \frac{[(\text{Control group score} - \text{treated group score}) \times 100]}{\text{Control group score}}$$

The percentage inhibitions for the various dose levels are plotted graphically for each compound. From these graphs the dosage required to achieve a 50% inhibition of the anaphylactic reaction ($ID_{50}$) may be determined.

The compounds are also evaluated in the above manner using intestinal gastric administration of the compound.

We claim:

1. A member selected from the group consisting of a compound of the formula

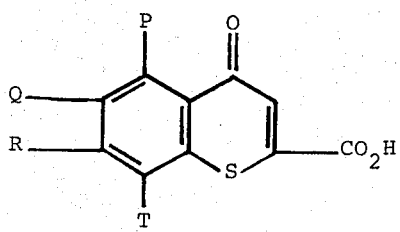

wherein P, Q, R, and T are the same or different and each represents hydrogen, alkyl, hydroxy, alkoxy, hydroxyalkoxy, alkoxyalkoxy, acetoxy, carboxy, amino, alkylamino, dialkylaminio, alkenyl, p-toluenesulfonyloxy, phenylalkyl, phenyl, nitro, carboxy ester derived from an alkanol of 1 to 6 carbon atoms, alkenyloxy, alkanoyl, none of which groups contain more tha 10 carbon atoms, or an adjacent pair of P, Q, R, and T form the chain —CH=CH—CH=CH—, with the provisos that
  i. not all of P, Q, R and T are hydrogen, and
  ii. when T is methoxy and Q and R are hydrogen, P is not a methyl group, and
a pharmaceutically acceptable salt thereof.

2. A compound according to claim 1 in which P, Q, R and T which may be the same or different, each represent hydrogen, an alkyl, hydroxy, alkoxy, hydroxyalkoxy, alkoxy-alkoxy, amino, alkylamino, dialkylamino, alkenyl, p-toluenesulphonyloxy, phenylalkyl, phenyl, nitro, carboxy ester group derived from an alkanol of 1 to 6 carbon atoms, or alkenyloxy groups none of which groups contain more than 10 carbon atoms.

3. A compound according to claim 1 in which P, Q, R and T, which may be the same or different, are hydrogen, hydroxyalkoxy, alkoxy-alkoxy, alkoxy, phenyl, alkyl, nitro, hydroxy, p-toluenesulphonyloxy or alkenyloxy none of which groups contain more than 10 carbon atoms.

4. A compound according to claim 1 in which P, Q, R and T represent hydrogen, methoxy, ethoxy, phenyl, allyloxy, isoamyloxy, methyl, propyl, t-butyl, p-toluenesulphonyloxy, or nitro.

5. A compound according to claim 1 which is 6-(2-Hydroxypropoxy)-1-thiachromone-2-carboxylic acid.

6. A compound according to claim 1 which is 6-(2-Ethoxyethoxy)-1-thiachromone-2-carboxylic acid.

7. A compound according to claim 1 which is 6-Ethoxy-1-thiachromone-2-carboxylic acid.

8. A compound according to claim 1 which is 5,8-Dimethoxy-1-thiachromone-2-carboxylic acid.

9. A compound according to claim 1 which is 5,8-Diethoxy-1-thiachromone-2-carboxylic acid.

10. A compound according to claim 1 which is 5:6-benzo-1-thiachromone-2-carboxylic acid.

11. A compound according to claim 1 which is 6-Phenyl-1-thiachromone 2-carboxylic acid.

12. A compound according to claim 1 which is 6-Methyl-1-thiachromone-2-carboxylic acid.

13. A compound according to claim 1 which is 6-Nitro-1-thiachromone-2-carboxylic acid.

14. A compound according to claim 1 which is 1-Thiachromone-2,8-dicarboxylic acid.

15. A compound according to claim 1 which is 6-Hydroxy-1-thiachromone-2-carboxylic acid.

16. A compound according to claim 1 which is 6-Allyloxy-1-thiachromone-2-carboxylic acid.

17. A compound according to claim 1 which is 6,8-Di-isopropyl-1-thiachromone-2-carboxylic acid.

18. A compound according to claim 1 which is 6-(3-Methoxybutoxy)1-thiachromone-2-carboxylic acid.

19. A compound according to claim 1 which is 5-(3-Methoxybutoxy)-8-propyl-1-thiachromone-2-carboxylic acid.

20. A compound according to claim 1 which is 5-(3-Methylbutoxy)-8-methyl-1-thiachromone-2-carboxylic acid.

21. A compound according to claim 1 which is 6,8-Di-t-butyl-1-thiachromone-2-carboxylic acid.

22. A compound according to claim 1 which is 8-Methyl-5-isopropyl-1-thiachromone-2-carboxylic acid.

23. A compound according to claim 1 which is 6-t-butyl-1-thiachromone-2-carboxylic acid.

24. A compound according to claim 1 which is 6-p-toluenesulphonyloxy-1-thiachromone-2-carboxylic acid.

* * * * *